US007709195B2

(12) United States Patent
Segawa et al.

(10) Patent No.: US 7,709,195 B2
(45) Date of Patent: May 4, 2010

(54) HYBRIDIZATION DETECTING UNIT RELYING ON DIELECTROPHORESIS AND SENSOR CHIP PROVIDED WITH THE DETECTING UNIT

(75) Inventors: Yuji Segawa, Tokyo (JP); Noriyuki Kishii, Kanagawa (JP)

(73) Assignee: Sony Corporation, Tokyo (JP)

(*) Notice: Subject to any disclaimer, the term of this patent is extended or adjusted under 35 U.S.C. 154(b) by 179 days.

(21) Appl. No.: 11/221,940

(22) Filed: Sep. 9, 2005

(65) Prior Publication Data

US 2006/0063183 A1 Mar. 23, 2006

(30) Foreign Application Priority Data

Sep. 15, 2004 (JP) .......................... P2004-268646

(51) Int. Cl.

*C12Q 1/68* (2006.01)
*C12N 11/16* (2006.01)
*G01N 15/06* (2006.01)
*C07H 21/04* (2006.01)

(52) U.S. Cl. .................... 435/6; 435/283.1; 435/287.2; 422/68.1; 422/82.01; 536/23.1

(58) Field of Classification Search ...................... None
See application file for complete search history.

(56) References Cited

U.S. PATENT DOCUMENTS

| | | | | |
|---|---|---|---|---|
| 6,099,803 | A * | 8/2000 | Ackley et al. | 422/68.1 |
| 6,290,839 | B1 * | 9/2001 | Kayyem et al. | 205/777.5 |
| 6,319,472 | B1 * | 11/2001 | Ackley et al. | 422/68.1 |
| 7,435,384 | B2 * | 10/2008 | Fish | 422/82.02 |
| 2005/0112548 | A1 * | 5/2005 | Segawa et al. | 435/4 |
| 2005/0112645 | A1 * | 5/2005 | Segawa et al. | 435/6 |
| 2005/0274612 | A1 * | 12/2005 | Segawa et al. | 204/403.01 |
| 2006/0127904 | A1 * | 6/2006 | Segawa et al. | 435/6 |

FOREIGN PATENT DOCUMENTS

| | | |
|---|---|---|
| JP | 2003-75302 | 3/2003 |
| JP | 2004-135512 | 5/2004 |
| WO | WO 96/42013 | 12/1996 |

OTHER PUBLICATIONS

Seiichi Suzuki et al., "Quantitative Analysis of DNA Orientation in Stationary AC Electric Fields Using Fluorescence Anisotropy," IEEE Transactions on Industry Applications, vol. 34, No. 1, pp. 75-83 (1998).
Masao Washizu, "DNA Handling under Visual Observation," Visualized Information, vol. 20, No. 76 (2000).
Masao Washizu et al., "Electrostatic Manipulation of DNA in Microfabricated Structures," IEEE Transactions on Industry Applications, vol. 26, No. 6, pp. 1165-1172 (1990).

* cited by examiner

*Primary Examiner*—B J Forman
(74) *Attorney, Agent, or Firm*—Finnegan, Henderson, Farabow, Garrett & Dunner, L.L.P.

(57) ABSTRACT

A hybridization detecting unit which includes a reaction region in which hybridization takes place, a plurality of sites (e.g., the surface of electrodes) arranged in the reaction region to which is fixed a nucleic acid for detection, and means for sequentially moving by dielectrophoresis the target nucleic acid introduced into the reaction region according to the order of arrangement of the sites to which is fixed a nucleic acid for detection. A sensor chip provided with the hybridization detecting unit. The detecting unit compulsorily moves the target nucleic acid into the region where a probe nucleic acid for detection exists, thereby increasing the probability of hybridization taking place.

13 Claims, 7 Drawing Sheets

HYBRIDIZATION DETECTING UNIT RELYING ON DIELECTROPHORESIS AND SENSOR CHIP PROVIDED WITH THE DETECTING UNIT

BACKGROUND OF THE INVENTION

The present invention relates to a technique to detect hybridization. More particularly, the present invention relates to a technique to detect hybridization which is so designed as to move by dielectrophoresis a target nucleic acid to a site where a nucleic acid for detection is fixed.

It has recently become common practice to use an integrated substrate for bioassay which has DNA molecules of prescribed species minutely arranged thereon by microarray technology. The integrated substrate, which is called DNA chip or DNA microarray (the former terminology is used in the present invention), is used to analyze gene mutation, SNPs (simple nucleotide polymorphism), and gene expression frequency. It will find use in broad areas including drug development, clinical diagnosis, pharmacogenomics, evolution research, and legal medicine.

The DNA chip is a glass substrate or silicon substrate on which are integrated a variety of and a large number of DNA oligochains or cDNA (complementary DNA). Consequently, the DNA chip of the invention permits comprehensive analysis of hybridization. The background and related art of the present invention will be described in the following.

JP-A-2001-507441 discloses a tiny electrophoresis chip which is designed to move or separate charged molecules such as nucleic acid, through a channel formed in a substrate, the channel having tiny electrodes arranged therein which produce an electric field to move or separate the charged molecules in the channel. This related art technology suggests that electrophoresis is commonly used to move or separate charged molecules such as nucleic acid.

Japanese Patent Laid-open No. 2003-75302 (particularly claim 1 and Paragraph 0027) discloses an apparatus to move a charged substance with polarity. This apparatus consists of a substrate and a plurality of electrodes arranged in a prescribed direction. A voltage with a reverse polarity of the charged substance is applied to a section of the electrodes. This procedure is repeated sequentially for adjacent sections, so that the charged substance is moved in the direction in which the electrodes are arranged. Further, the configuration in which a surface of an electrode to be used is covered with an insulating film is also disclosed.

Japanese Patent Laid-open No. 2004-135512 discloses an apparatus which has scanning electrodes arranged in the reaction region, such that when a voltage is applied across adjacent electrodes, nucleic acid molecules are attracted and fixed to the electrode edges as if they span from one electrode to another.

SUMMARY OF THE INVENTION

The DNA chip technology which has been proposed so far is designed to analyze hybridization that takes place between a nucleic acid for detection and a target nucleic acid complementary thereto in a reaction region for hybridization formed on a substrate, the reaction region having a nucleic acid for detection (such as probe DNA) fixed therein.

The disadvantage of the conventional DNA chip technology is that the probability of the target nucleic acid meeting its complementary nucleic acid for detection is very low under the natural condition in which Brownian motion is the only driving force. This is true particularly in the case where the amount of the target nucleic acid is very small in the sample solution to be dropped into the reaction region. This presents difficulties in detecting the target nucleic acid or difficulties in accurately determining the amount of the target nucleic acid even though the detection of the target nucleic acid is possible.

Thus, it is an object of the present invention to provide a technique to increase the probability of occurrence of hybridization by moving the target nucleic acid compulsorily into the region where a nucleic acid for detection (or a probe nucleic acid) exists.

The present invention is directed to a hybridization detecting unit and a sensor chip provided with the detecting unit. The hybridization detecting unit includes a reaction region in which hybridization takes place, a plurality of sites arranged in the reaction region to which is fixed a nucleic acid for detection, and means for sequentially moving by dielectrophoresis the target nucleic acid introduced into the reaction region according to the order of arrangement of the sites to which is fixed a nucleic acid for detection.

According to the present invention, the hybridization detecting unit ("detecting unit" for short hereinafter) is characterized in that the target nucleic acid introduced somehow into the reaction region is driven by dielectrophoresis which produces an electrodynamic action. "Dielectrophoresis" is a phenomenon that an applied electric field and its induced polarization vector (electric dipole) apply a force to a substance (nucleic acid molecules in the present invention) through their mutual action. Thus, dielectrophoresis moves a substance toward a part (such as a tiny electrode) to which the lines of electric force converges in the reaction region in which electrodes are so arranged as to form uneven electric fields. The action of dielectrophoresis on nucleic acid molecules is mentioned in Non-Patent Document 1 (Seiichi Suzuki, Takeshi Yamanashi, Shin-ichi Tazawa, Osamu Kurosawa and Masao Washizu: "Quantitative analysis on electrostatic orientation of DNA in stationary AC electric field using fluorescence anisotropy", IEEE Transaction on Industrial Applications, vol. 34, No. 1, p. 75 to 83 (1998)) and Non-Patent Document 2 (Masao Washizu: "DNA Handling under visual observation", Visualized Information, vol. 20, No. 76 (January 2000). These documents will help fully understand the present invention.

The above-mentioned detecting unit according to the present invention has a plurality of sites arranged in the reaction region to which is fixed a nucleic acid for detection (Such sites may be the surfaces of electrodes). The fixing sites are sequentially energized in the order of their arrangement, so that the induced electrodynamic force sequentially drives the target nucleic acid toward the vicinity of the fixing sites, thereby increasing the probability of the target nucleic acid meeting the nucleic acid for detection on the fixing sites. Incidentally, it is desirable to cover by an insulating film the electrode surface in the case where the electrode surface is used as the site to which is fixed the nucleic acid for detection. The cover protects the electrode from electrochemical reactions by ionic solutions which might remain in the reaction region.

The detecting unit may have electrode surfaces (facing each other through the reaction region), either or both of which function as the site where the nucleic acid for detection is fixed.

The opposing electrodes may be constructed such that either of them is a single common electrode or a set of discrete common electrodes. Alternatively, they may be constructed of more than one pair of opposing electrodes which may be arranged symmetrically. They should be arranged such that an electric field is applied across the first pair of opposing electrodes and then across the second pair of opposing electrodes and so on in the order in which they are arranged.

According to the present invention, the assay system for hybridization may be constructed in any of the following three ways.

(A) All of the fixing sites are used to fix the detecting nucleic acid of the same species.

(B) Each of the fixing sites is use to fix the detecting nucleic acid of different species.

(C) The fixing sites are divided into a predetermined number of groups and each group is used to fix the detecting nucleic acid of different species.

The second and third constructions are desirable in the case where the reaction region contains more than one species of target nucleic acid. In this case, hybridization starts at the site (or the group of sites) near the entrance and propagates sequentially.

"Dielectrophoresis" as used in the present invention should preferably be an electrodynamic effect which is produced by application of AC electric field (particularly high-frequency one) to the medium retained or held in the reaction region. Unlike a DC electric field, an AC electric field does not produce any adverse effect due to electrolysis.

The present invention is directed also to a method for detecting hybridization which includes a first step of fixing one or more than one species of nucleic acid for detection to a plurality of fixing sites in the reaction region in which hybridization takes place, a second step of introducing a target nucleic acid into the reaction region, and a third step of allowing hybridization to proceed while sequentially moving the target nucleic acid toward the selected fixing sites by dielectrophoresis.

The first step is intended to chemically bond the terminals of nucleic acid for detection (as a probe) to prescribed fixing sites. The chemical bonding for fixing is not specifically restricted. Fixing may be accomplished through linker molecules if necessary. In the case where the electrode surface is used as the fixing site, it is possible to promote fixing by application of an electric field for dielectrophoresis that attracts the nucleic acid for detection to the electrode edge.

The second step is intended to introduce the target nucleic acid (or a medium thereof) into the reaction region. The procedure and means for introduction are not specifically restricted. They may be properly selected according to the construction of the reaction region and the physical properties of the medium.

The third step is intended to cause hybridization to proceed sequentially at the fixing sites arranged in the reaction region. In the third step, the target nucleic acid is allowed to move toward the vicinity of the prescribed fixing site where hybridization takes place. This step is repeated until hybridization takes place at all the fixing sites. Movement of the target nucleic acid is caused by dielectrophoresis.

Technical terms used in the present invention are defined as follows.

"Nucleic acid" denotes a polymer of a phosphate ester of nucleoside composed of purine or pyrimidine base and sugar which are bonded together through glycoside linkage (The polymer is a nucleotide chain). It broadly embraces oligonucleotide (including probe DNA), polynucleotide, DNA (and fragments thereof) formed by polymerization of purine nucleotide and pyrimidine nucleotide, cDNA (or c-probe DNA) obtained by reverse transcription, RNA, and polyamide nucleotide derivative (PNA).

"Nucleic acid for detection" denotes a nucleic acid which functions as a probe to detect a target nucleic acid having a complementary base sequence that reacts specifically with the nucleic acid. The nucleic acid may be present in a fixed state or free state in the medium retained or held in the reaction region. The nucleic acid is often called a probe. Its typical examples are oligonucleotide (probe DNA) and polynucleotide.

"Target nucleic acid" denotes a nucleic acid having a base sequence which is complementary to that of the nucleic acid for detection.

"Hybridization" denotes a reaction that forms a complementary chain (double-stranded chain) from chains having complementary base sequence. Incidentally, "mishybridization" denotes a reaction that forms an anomalous complementary chain.

"Reaction region" denotes a place where hybridization takes place. For example, a reaction region may be a well capable of retaining liquid or gel therein.

"Fixing site of nucleic acid for detection" denotes a site whose surface is so constructed as to permit direct or indirect chemical bonding between the site and the terminal of nucleic acid for detection.

"Opposing electrodes" denotes at least one pair of electrodes which are arranged such that their surfaces face each other. In the present invention, one of the electrodes may function as a common electrode. It should be noted that a "common electrode" denotes an electrode constituting the opposing electrodes in a plurality of electrodes.

"Intercalator" denotes a fluorescent substance that can be inserted into the double-stranded nucleic acid. This substance is used to detect hybridization. It includes, for example, POPO-1, TOTO-3, and SYBR (Registered Trademark) Green I.

"Steric hindrance" denotes a phenomenon that one molecule can hardly come close to the other molecule for reaction on account of a bulky substituent group present near the reaction center in the molecule or on account of the posture or stereostructure (high-order structure) of the molecule involved in reaction. Steric hindrance prevents the desired reaction (or hybridization in the present invention) from taking place easily.

"Dielectrophoresis" denotes a phenomenon that molecules in an uneven electric field are driven toward that part of the uneven electric field in which the electric field is strong. AC voltage produces this effect as DC voltage because the reversing polarity of AC voltage reverses the polarity of polarization (See "Micromachine and Material Technology" edited by Teru Hayashi, published by C.M.C., p. 37 to 46, Chapter 5 Cells and DNA manipulation).

"Sensor chip" broadly denotes the substrate for detection of hybridization on which the target nucleic aid (such as DNA probe) is fixed and microarrayed. It embraces the concept of DNA microarray.

The present invention is designed to compulsorily move by dielectrophoresis the target nucleic acid to the region in which the nucleic acid for detection is fixed. Movement in this way increases the probability that hybridization takes place. In addition, dielectrophoresis elongates the nucleic acid molecules, thereby reducing steric hindrance detrimental to hybridization or reducing mishybridization.

DETAILED DESCRIPTION OF THE PREFERRED EMBODIMENTS

The preferred embodiments of the present invention will be described in more detail with reference to the accompanying drawings, which are mere examples and should not be construed to restrict the scope of the present invention.

FIGS. 1 to 10 are diagrams illustrating the detecting unit pertaining to the preferred embodiments of the present invention. The substrate structure common to all the embodiments will be described with reference to FIG. 1 which is a vertical sectional view showing the detecting unit according to the first embodiment of the present invention.

The substrate that can be used in the present invention may be formed from the same material as used for optical information recording media, such as CD (Compact Disc), DVD (Digital Versatile Disc), and MD (Mini Disc). In addition, the substrate used in the present invention is not specifically restricted in its shape; it may assume any shape such as disc and rectangle depending on the object of their use.

Figure 1:
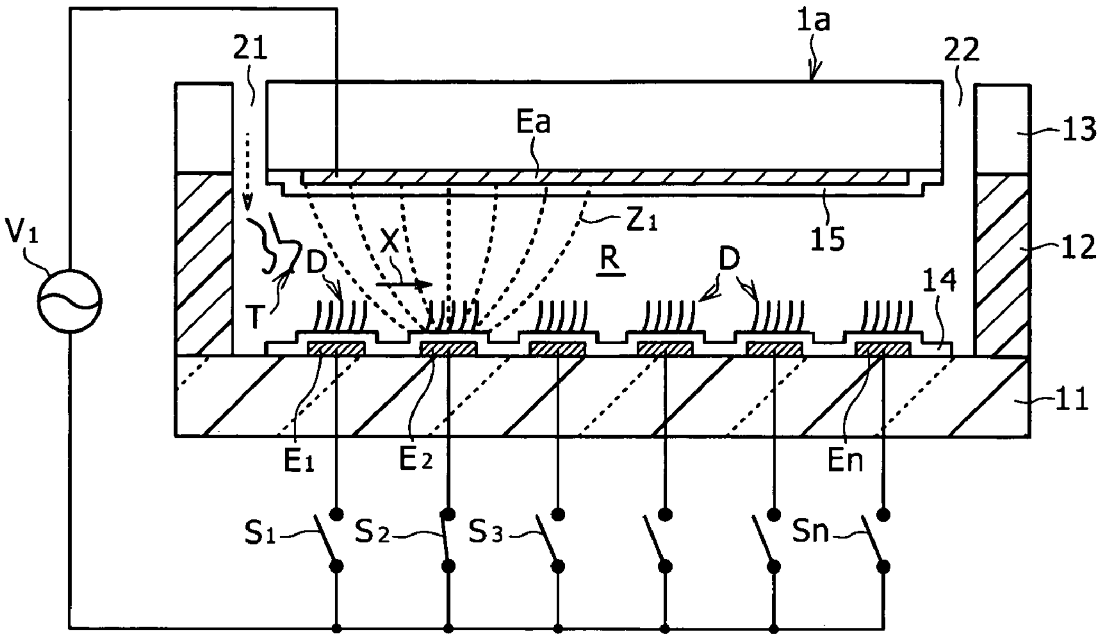
FIG. 1 is a vertical sectional view showing the detecting unit according to the first embodiment of the present invention.

The underlying substrate 11 (the lowermost layer) shown in FIG. 1 is formed from transparent silica glass or transparent synthetic resin (such as silicone, polycarbonate, and polystyrene). A synthetic resin capable of injection molding is desirable. The underlying substrate 11 of inexpensive synthetic resin is more economical than conventional glass chips.

The underlying substrate 11 shown in FIG. 1 is transparent to light of specific wavelength. Therefore, it facilitates the detection of fluorescence in the reaction region (R) by photoirradiation from below (or through the back side). It also permits transmission of fluorescence exciting light and excited fluorescence and transmission of light to detect the position of the reaction region and light for focusing.

The transparent underlying substrate 11 may be of double-layer structure (not shown). In this case, the upper layer should have a higher refractive index than the lower layer and medium, so that focus servo control and positioning servo control are accomplished accurately and rapidly.

The underlying substrate 11 constructed as mentioned above so that fluorescence in the reaction region (R) is detected by photoirradiation from below offers the following advantage when devices are arranged around the detecting unit. That is, the space above the substrate may be allocated to devices for dropping or injecting a sample solution and the space below the substrate is allocated to optical devices for detection (or reading).

On the underlying substrate 11 is the reaction region defining layer 12 which is formed from synthetic resin (such as photosensitive polyimide resin) by any known optical disc mastering technique. The reaction region defining layer 12 defines the well-like reaction region (R) in which hybridization takes place. Incidentally, the shape of the reaction region (R) is not limited to "well".

On the reaction region defining layer 12 is the upper layer 13, which has at least a light reflecting layer or thin film (not shown), a few nanometers to tens of nanometers in thickness.

It is desirable that the substrate used in the present invention should previously undergo surface treatment with an agent that makes the surface (including the surface in the reaction region (R)) compatible with the medium. In other words, the surface should be divided into hydrophilic parts and hydrophobic parts, so that a living body substance of interest can be smoothly introduced into the reaction region (R). The above-mentioned layer structure of the substrate is applicable to all the embodiments that will be mentioned in the following.

The detecting unit according to the present invention is constructed as described below with reference to the accompanying drawings. The first embodiment shown in FIG. 1 is constructed as follows.

FIG. 1 is a vertical sectional view showing the detecting unit (symbol 1$a$) according to the first embodiment of the present invention. The detecting unit 1$a$ consists of one tiny detecting region or a plurality of tiny detecting regions arranged on a substrate of prescribed shape. (This is applicable to other detecting units.) The detecting unit 1$a$ has the reaction region (R) for hybridization to take place, which retains an aqueous solution (such as buffer solution) containing a sample or which holds gel (such as agarose gel).

A number of detecting units 1$a$ may be arranged on the substrate such that they can be easily grouped according to the object of assay. For example, they may be grouped according to the kind of sample substance and the type of gene.

The reaction region (R) formed in the detecting unit 1$a$ is not specifically restricted in shape and size. It measures a few micrometers to hundreds of micrometers in length, width, and depth. The actual dimensions are determined according to the spot diameter of exciting light and the minimum amount of sample solution (containing detecting nucleic acid and target nucleic acid) that can be dropped (This is applicable to other detecting units). In addition, the detecting unit may be constructed such that a plurality of reaction regions communicate with one another (not shown).

There are shown openings 21 and 22 in FIG. 1. One of them serves as an entrance for the medium containing a target nucleic acid (T) or an intercalator. The other serves as an air vent. The medium may be introduced by means of capillary action.

In the reaction region (R) constituting the detecting unit 1*a* are arranged the sites to which are fixed the terminals of the detecting nucleic acid (D), such as DNA probe. They will be referred to as "fixing sites" for short hereinafter. The larger the number and area of fixing site, the larger the amount of hybridization.

The fixing site should have a surface structure that permits the terminals of the detecting nucleic acid molecules (D) to be fixed. It is desirable to use the electrode surface as the fixing site as indicated by symbols $E_1$ to $E_n$ in FIG. 1, because this construction permits electric field (particularly dielectrophoresis) to be used when the detecting nucleic acid (D) is fixed. FIG. 1 schematically shows the fixing sites $E_1$ to $E_n$ arranged at certain intervals on the lower surface of the reaction region (R), each site having a predetermined amount of detecting nucleic acid (D) fixed thereto.

The fixing sites $E_1$ to $E_n$, to which are fixed the terminals of the detecting nucleic acid (D), should previously be surface-treated with a solution of silane coupling agent containing amino groups or a solution of polylysine. In the case of synthetic resin substrates, the surface treatment should be preceded by plasma treatment, irradiation with deep ultraviolet rays or far infrared rays.

The above-mentioned surface treatment may be replaced by film coating with copper, silver, aluminum, or gold by sputtering, and the resulting metal film is further coated with a substance having amino groups, thiol groups, or carboxyl groups, or with cysteamine or streptavidin. Surface treatment with streptavidin is suitable for the terminals of biotylated DNA probe to be fixed. Surface treatment with thiol groups (SH) is useful in the case where the detecting substance (D), such as thiol-modified probe DNA, is to be fixed through a disulfide linkage (—S—S— linkage).

It is desirable to prevent the detecting nucleic acid (D) from sticking to that part of the detecting surface other than the detecting sites. This object is achieved by fixing the detecting nucleic acid (D) to each of the fixing sites ($E_1$ to $E_n$), with a linker molecule or spacer molecule interposed between them. The interposing molecule provides a certain distance between the fixing site and the detecting nucleic acid. In addition, interposing molecules varying in length prevent the detecting nucleic acid molecules (D), which are fixed to the fixing sites $E_1$ to $E_n$, from interfering with one another. The length of the interposing molecules should be properly determined according to the length (the number of bases) of the detecting nucleic acid (D) or the target nucleic acid (T), or according to the distance between the adjacent molecules of the detecting nucleic acid (D).

The surface of the electrodes $E_1$ to $E_n$ in the detecting unit 1*a* functions as the fixing sites for the detecting nucleic acid D, as mentioned above. The electrodes $E_1$ to $E_n$ are arranged such that they face the common electrode $E_a$ placed above them, with the reaction region (R) interposed between them. See FIG. 1. In other words, there exist n opposing electrodes $E_1$-$E_a$ to $E_n$-$E_a$ in the reaction region.

The electrodes $E_1$ to $E_n$ should preferably be formed from a metal, such as aluminum and gold, or a transparent conducting material, such as ITO (indium-tin oxide). The latter facilitates detection by light from below through the back side of the underlying substrate 11.

The electrodes $E_1$ to $E_n$ should preferably be covered with an insulating film 14 formed from any of $SiO_2$, SiC, SiN, SiOC, SiOF, and $TiO_2$. Likewise, the common electrode $E_a$ should also be covered with an insulating film 15 of the same material as mentioned above. The insulating film prevents electrochemical reactions induced by an ionic solution retained in the reaction region (R).

The opposing electrodes $E_1$-$E_a$ to $E_n$-$E_a$ apply electric fields continuously or intermittently to the reaction region R (or the medium therein) as their switches $S_1$ to $S_n$ are properly turned on and off.

Sequential application of electric field to the opposing electrodes $E_1$-$E_a$ to $E_n$-$E_a$ moves continuously or intermittently the target nucleic acid T, which has been introduced from the opening 21, in the direction of arrow X by the action of dielectrophoresis which is produced by the uneven electric field it the vicinity of each electrode $E_1$ to $E_n$ (which are smaller than the common electrode $E_a$) (The uneven electric field includes one in which the intensity of electric field has a steep gradient). Incidentally, FIG. 1 schematically shows the electric flux lines (Z) which suggest that an electric field has been formed between the opposing electrodes $E_2$-$E_a$, with the switch $S_2$ turned on.

As the result, the target nucleic acid (T) moves, sequentially passing through the vicinities of the electrodes $E_1$ to $E_n$. In this process, hybridization takes place sequentially between the target nucleic acid (T) and the detecting nucleic acid (D) which is fixed to the electrodes $E_1$ to $E_n$. If necessary, application of electric field may be repeated to move the target nucleic acid (T) for complete hybridization.

Incidentally, application of AC electric field (particularly application of high-frequency AC electric field under specific conditions) induces dielectrophoresis which, owing to its electrodynamic effect, causes the nucleic acid molecules (both the detecting nucleic acid D and the target nucleic acid (T)) to linearly grow while moving them in the reaction region (R).

Application of electric field loosens the high-order structure of nucleic acid molecules and stretches nucleic acid molecules and moves nucleic acid molecules to the desired region, thereby increasing the probability of nucleic acid molecules meeting each other. In the absence of electric field, hybridization takes place between single-stranded nucleic acid molecules which are randomly coiled or twisted. Nucleic acid molecules under such conditions are subject to mishybridization on account of steric hindrance and inefficient complementary binding.

Application of electric field stretches the fixed nucleic acid molecules on account of the action of dielectrophoresis, thereby reducing the effect of steric hindrance and greatly improving the efficiency and accuracy of hybridization. This leads to the rapid detection of hybridization. It is not always necessary to apply electric field continuously. It is permissible to turn off electric field intermittently so that hybridization of nucleic acid molecules proceeds as the result of natural Brownian movement.

When to turn on and off the switches $S_1$ to $S_n$ depends on the object and desired effect of hybridization. Sequentially turning on the switches $S_1$ to $S_n$ causes the target nucleic acid (T) to move continuously from one electrode to its adjacent electrode. Sequentially turning on and off the switches $S_1$ to $S_n$ causes the target nucleic acid (T) to move intermittently from one electrode to its adjacent electrode.

The detecting unit should preferably be constructed such that the intensity of electric field can be selected for the opposing electrodes $E_1$-$E_a$ to $E_n$-$E_a$ individually, the power source can be selected from AC and DC, and the electric field can be selected from high-frequency one and low-frequency one (This shall apply to other embodiments). Such construction is adaptable to various conditions for hybridization and electric field.

The detecting unit according to the second embodiment of the present invention will be described below with reference to FIG. 2.

Figure 2:
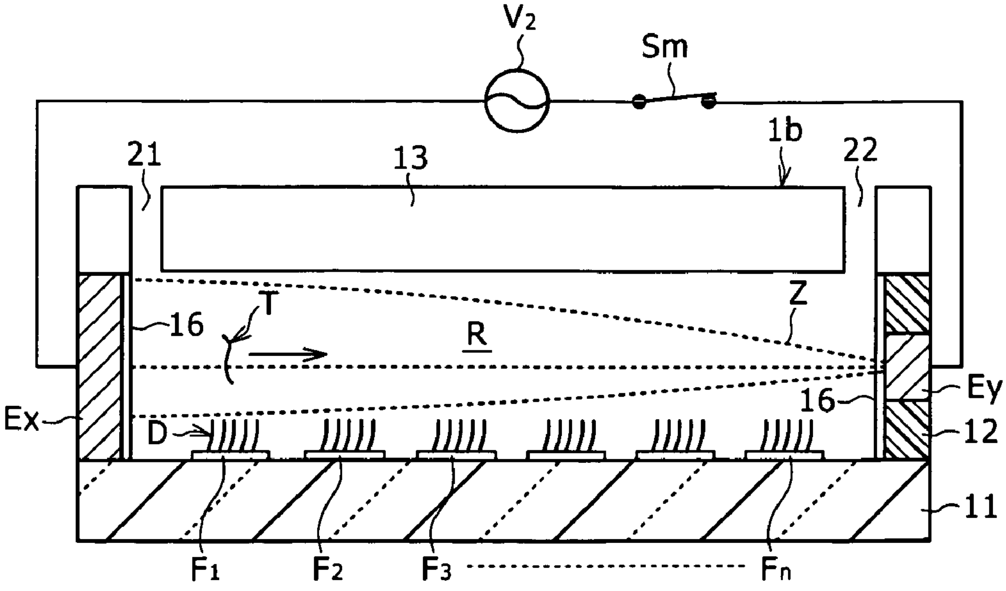
FIG. 2 is a vertical sectional view showing the detecting unit according to the second embodiment of the present invention.

The detecting unit (indicated by symbol 1*b*) in FIG. 2 differs in construction from the detecting unit 1*a* according to the first embodiment such that the fixing sites indicated by symbols $F_1$ tos $F_n$ are not electrodes and the reaction region (R) is provided with opposing electrodes $E_x$-$E_y$ at its right and left sides (Compare FIG. 1 with FIG. 2).

The detecting unit 1*b* produces an electric field that extends from left to right along the fixing sites $F_1$ to $F_n$ when an electric field is applied to the opposing electrodes $E_x$-$E_y$. If either of the opposing electrodes is made smaller than the other, an uneven electric field is produced in the vicinity of the smaller electrode (Ey, in this case). Incidentally, symbol Z in FIG. 2 schematically shows the line of electric force due to such an uneven electric field.

The target nucleic acid T, which is present in a free state in the reaction region (R), is moved toward the uneven electric field by the action of dielectrophoresis. During its movement, it experiences hybridization with the detecting nucleic acid D fixed to each of the fixing sites $F_1$ to $F_n$. Incidentally, the switch $S_m$ shown in FIG. 2 may be turned on continuously or intermittently.

The detecting unit according to the third embodiment of the present invention will be described below with reference to FIG. 3.

Figure 3:
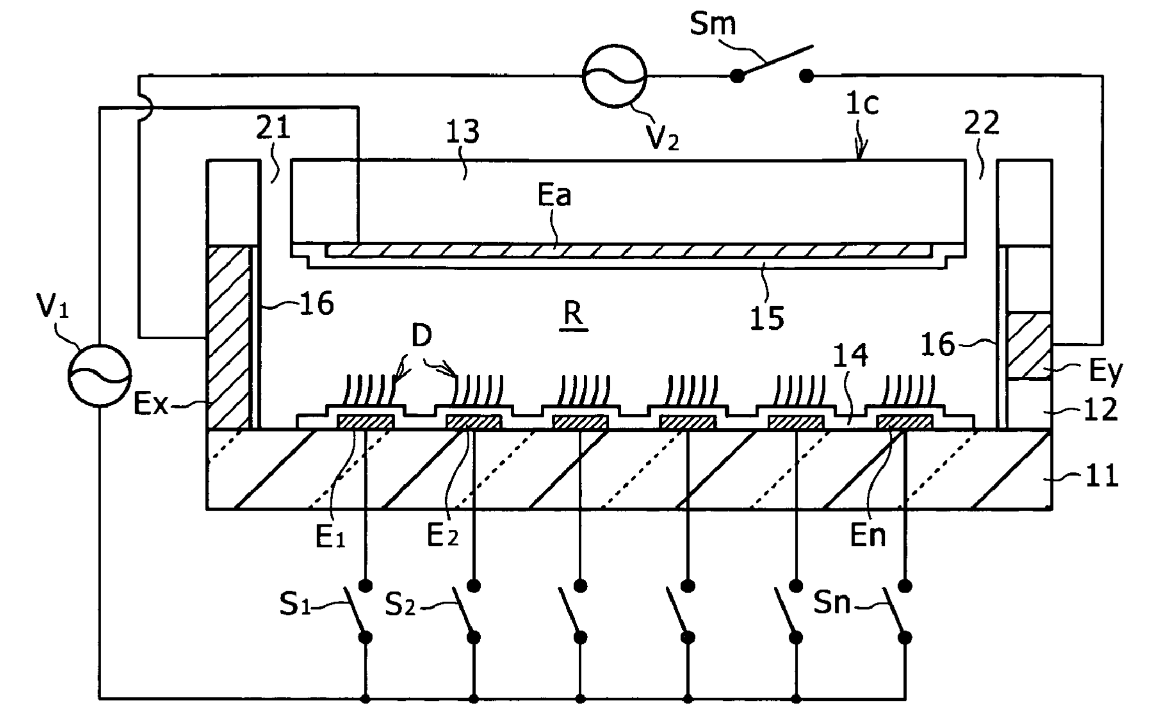
FIG. 3 is a vertical sectional view showing the detecting unit according to the third embodiment of the present invention.

The detecting unit 1*c* shown in FIG. 3 is characterized in that it has the opposing electrodes $E_1$-$E_a$, to $E_n$-$E_a$, which are arranged above and below the reaction region (R), and the opposing electrodes $E_x$-$E_y$, which are arranged at right and left of the reaction region (R). The detecting unit 1*c* is, so to speak, a combination of the detecting unit 1*a* shown in FIG. 1 and the detecting unit 1*b* shown in FIG. 2.

The advantage of the detecting unit 1*c* is that the target nucleic acid T is moved to the vicinity of the desired position by application of an electric field to the opposing electrodes $E_x$-$E_y$ and then attracted to the vicinity of the electrodes $E_1$ to $E_n$ by application of an electric field to the opposing electrodes $E_1$-$E_a$ to $E_n$-$E_a$. Another advantage is that the opposing electrodes $E_x$-$E_y$ may be used to eliminate any substance detrimental to hybridization and nucleic acid molecules that have undergone mishybridization from the reaction region.

The detecting unit according to the fourth embodiment of the present invention will be described below with reference to FIG. 4, which is a vertical sectional view.

Figure 4:
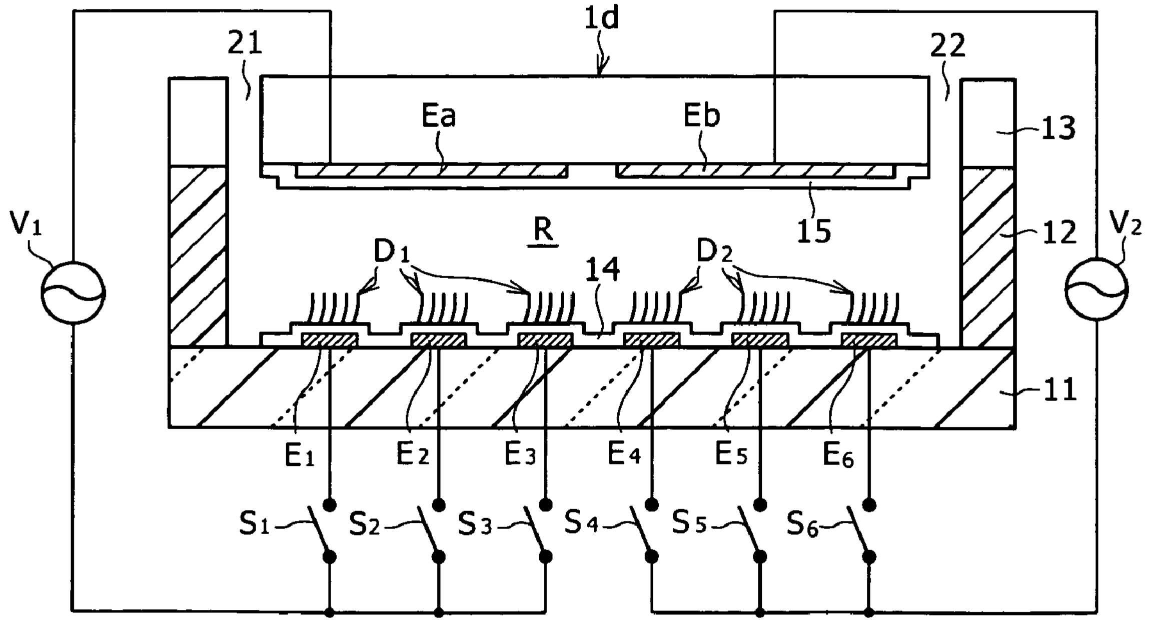
FIG. 4 is a vertical sectional view showing the detecting unit according to the fourth embodiment of the present invention.

The detecting unit 1*d* shown in FIG. 4 is characterized in that it has more than one set of opposing electrodes (two sets in this case, one consisting of $E_1$-$E_a$, $E_2$-$E_a$, and $E_3$-$E_a$ and the other consisting of $E_4$-$E_b$, $E_5$-$E_b$, and $E_6$-$E_b$). Each group of the opposing electrodes is connected to separate power sources $V_1$ and $V_2$, so that an electric field can be applied to them independently.

The detecting unit 1*d* shown in FIG. 4 has six lower electrodes; however, the number of electrodes and the number of sets of opposing electrodes may be selected as desired.

The detecting nucleic acid $D_1$ can be fixed to one group of the opposing electrodes $E_1$-$E_a$, $E_2$-$E_a$, and $E_3$-$E_a$, and the detecting nucleic acid $D_2$ is fixed to the other group of the opposing electrodes $E_1$-$E_b$, $E_2$-$E_b$, and $E_3$-$E_b$. However, it is possible to fix the detecting nucleic acid D of the same species to all of the electrodes $E_1$ to $E_6$.

The detecting unit according to the fifth embodiment of the present invention will be described below with reference to FIG. 5, which is a vertical sectional view.

Figure 5:
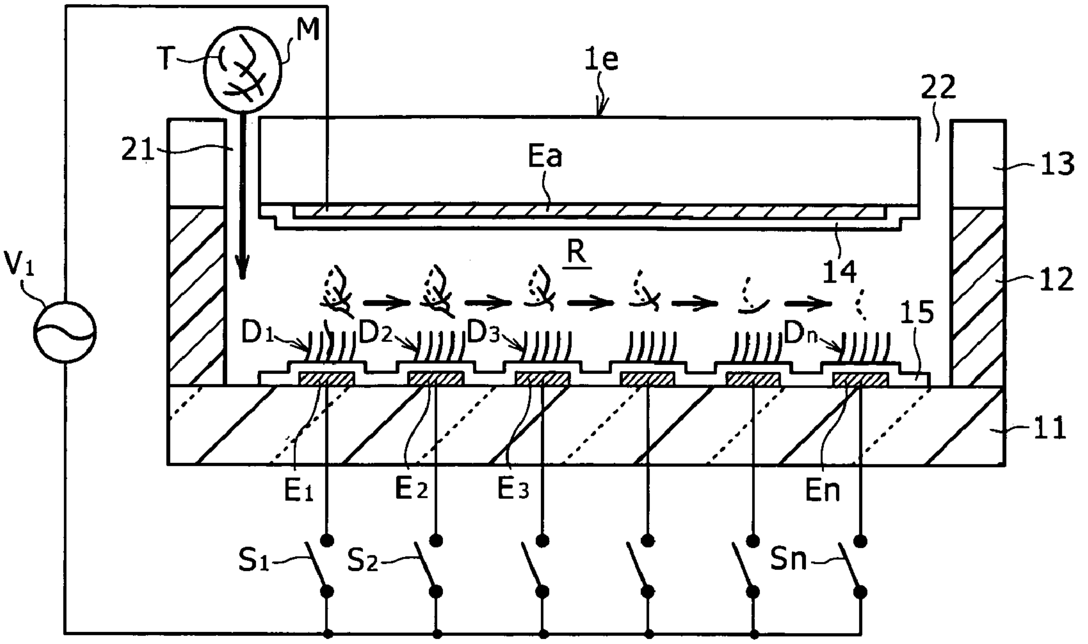
FIG. 5 is a vertical sectional view showing the detecting unit according to the fifth embodiment of the present invention.

The detecting unit 1*e* shown in FIG. 5 is characterized in that the detecting nucleic acids $D_1$ to $D_n$ (which are different in base sequence) are fixed respectively to the electrodes $E_1$ to $E_n$ which function as the fixing sites.

The detecting unit 1*e* constructed as mentioned above moves the target nucleic acids (T) of different species contained in the medium M (which have been introduced through the opening 21) in the direction along the electrodes $E_1$ to $E_n$ (arranged from near to the opening 21 to further) as the switches $S_1$ to $S_n$ are turned on and off to apply electric field. During their movement, the target nucleic acids undergo hybridization sequentially. FIG. 5 schematically shows that the detecting nucleic acids $D_1$ to $D_n$ sequentially undergo hybridization with their complementary target nucleic acid T (from left to right).

Figure 6:
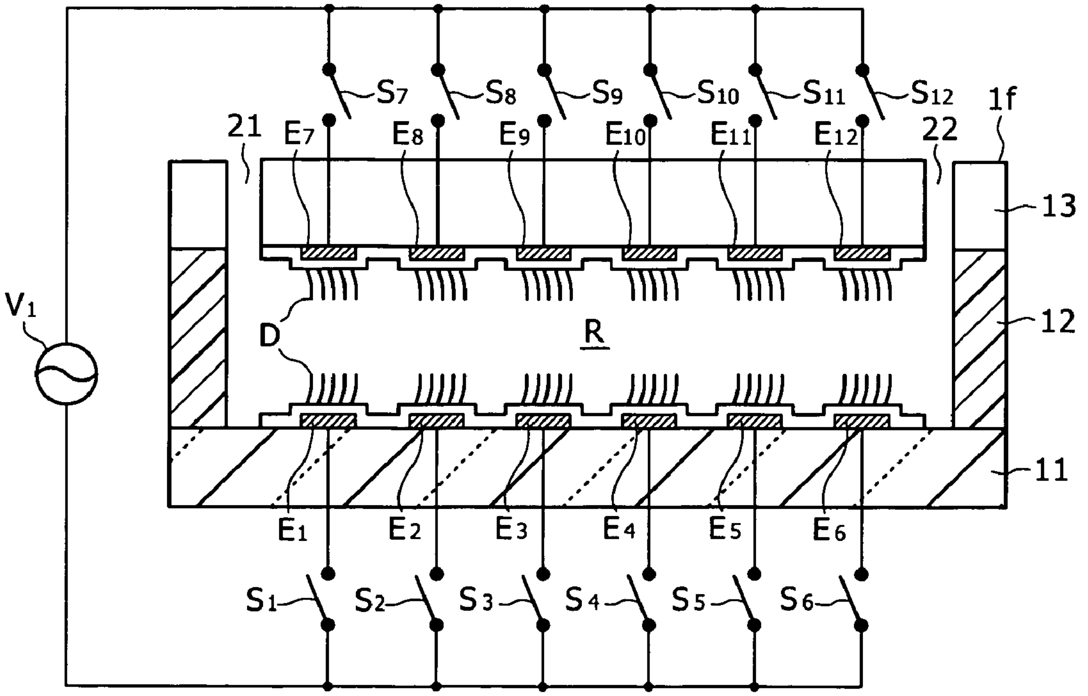
FIG. 6 is a vertical sectional view showing the detecting unit according to the sixth embodiment of the present invention.

The detecting unit according to the sixth embodiment of the present invention will be described below with reference to FIG. 6, which is a vertical sectional view.

The detecting unit 1*f* shown in FIG. 6 has several pairs (six pairs in this case) of opposing electrodes $E_1$-$E_7$, $E_2$-$E_8$, $E_3$-$E_9$, $E_4$-$E_{10}$, $E_5$-$E_{11}$, and $E_6$-$E_{12}$ which are symmetrically arranged at regular intervals above and below the reaction region (R).

To operate the detecting unit 1*f*, the paired switches ($S_1$-$S_7$, $S_2$-$S_8$, $S_3$-$S_9$, $S_4$-$S_{10}$, $S_5$-$S_{11}$, and $S_6$-$S_{12}$) are turned on and off sequentially in the ascending or descending order. Application of electric fields in this manner permits efficient hybridization at individual electrodes $E_1$ to $E_n$. It is also possible to apply an electric field across diagonally arranged electrodes (say, $E_1$ and $E_8$).

Figure 7A:
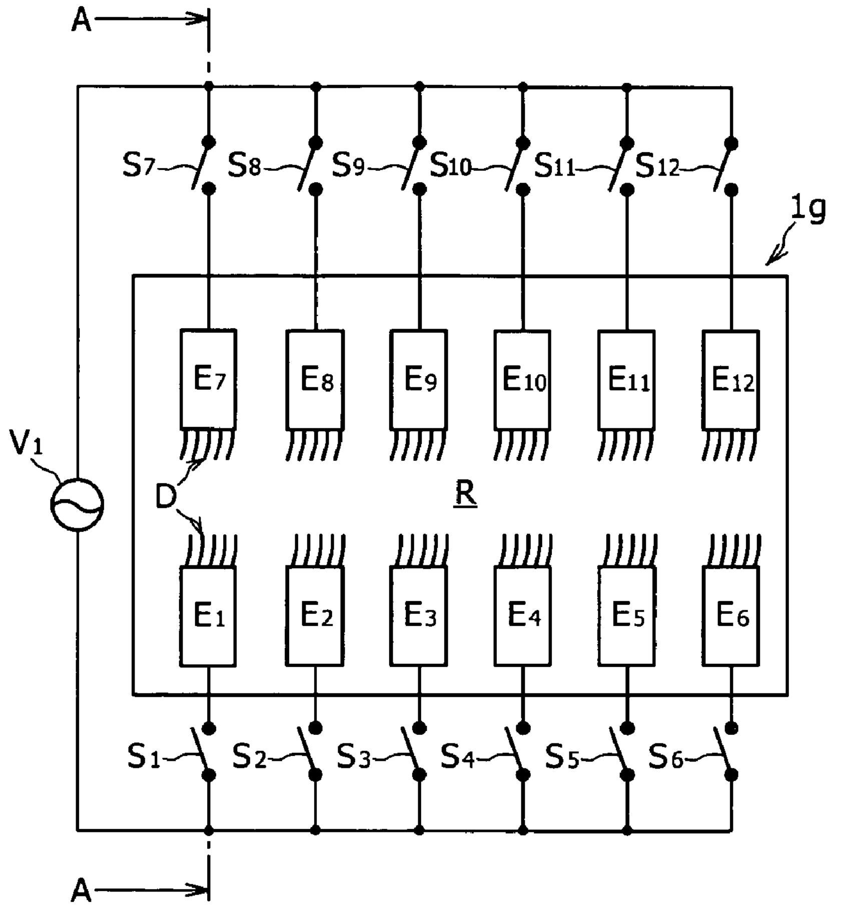
FIG. 7A is a diagram-showing the detecting unit according to the seventh embodiment of the present invention and it is a plan view of the reaction region in its open state.
Figure 7B:
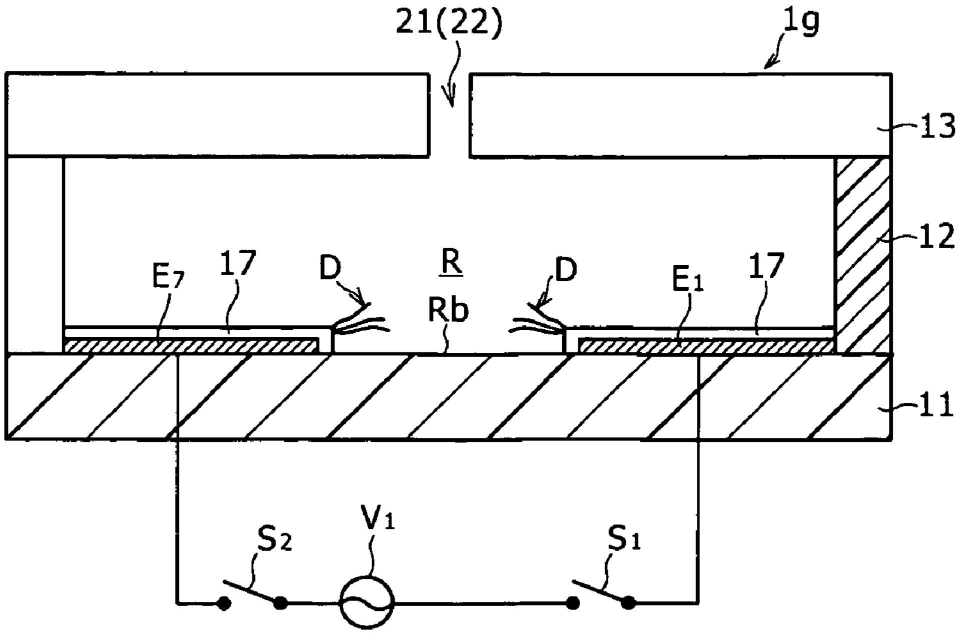
FIG. 7B is a vertical sectional view taken along the line A-A in the direction of arrows in FIG. 7A.

The detecting unit according to the seventh embodiment of the present invention will be described below with reference to FIGS. 7A and 7B. FIG. 7A is a plan view of the reaction region (R) in its open state. FIG. 7B is a sectional view taken along the line A-A in the direction of arrows in FIG. 7A.

The detecting unit 1*g* shown in FIGS. 7A and 7B is, so to speak, a modification of the above-mentioned detecting unit 1*f* according to the sixth embodiment. To be concrete, the detecting unit 1*g* has symmetrically arranged opposing electrodes like the detecting unit 1*f*. The difference between them is that all of the electrodes $E_1$ to $E_{12}$ are placed on the bottom (Rb) of the reaction region (R), as shown in FIG. 7B.

Incidentally, the symbol 17 in FIG. 7B denotes an insulating film formed from any of $SiO_2$, SiC, SiN, SiOC, SiOF, and $TiO_2$. FIGS. 7A and 7B schematically show the detecting nucleic acid D whose terminal is fixed to the edges of the opposing electrodes.

To operate the detecting unit 1*g*, the paired switches ($S_1$-$S_7$, $S_2$-$S_8$, $S_3$-$S_9$, $S_4$-$S_{10}$, $S_5$-$S_{11}$, and $S_6$-$S_{12}$) are turned on and off sequentially in the ascending or descending order. Application of electric fields in this manner permits efficient hybridization at individual electrodes $E_1$ to $E_n$. It is also possible to apply an electric field across diagonally arranged electrodes (say, $E_1$ and $E_8$).

The detecting unit according to the eighth embodiment of the present invention will be described below with reference to FIG. 8, which is a plan view of the reaction region (R) in its open state.

Figure 8:
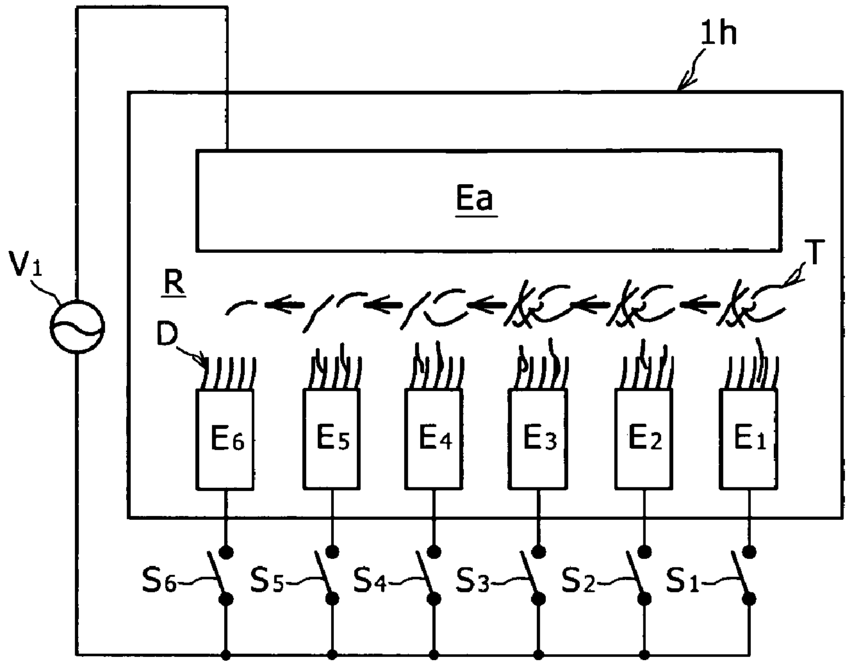
FIG. 8 is a diagram showing the structure of the detecting unit according to the eighth embodiment of the present invention and it is a plan view of the reaction region in its open state.

The detecting unit 1*h* shown in FIG. 8 is, so to speak, a modification of the above-mentioned detecting unit 1*a* according to the first embodiment. To be concrete, the detecting unit 1*h* has one common electrode $E_a$ and six electrodes $E_1$ to $E_6$ facing the common electrode $E_a$. All the electrodes are placed on the bottom $R_b$ of the reaction region (R).

In the detecting unit 1*h* shown in FIG. 8, the detecting nucleic acid D is fixed to each of the electrodes $E_1$ to $E_6$, as in the above-mentioned detecting unit 1*e* shown in FIG. 5. As the switches $S_1$ to $S_6$ are turned on sequentially, hybridization proceeds efficiently between the detecting nucleic acids D of different species, which are fixed to the electrodes $E_1$ to $E_6$, and the target nucleic acid T complementary to them.

The detecting unit according to the ninth embodiment of the present invention will be described below with reference to FIG. 9, which is a plan view of the reaction region (R) in its open state.

Figure 9:
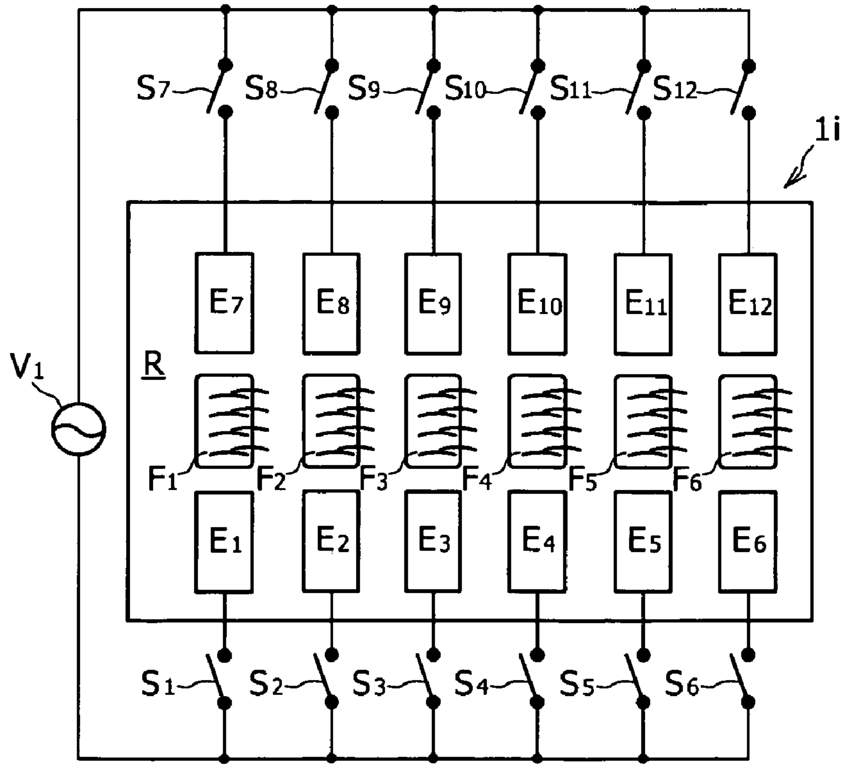
FIG. 9 is a diagram showing the structure of the detecting unit according to the ninth embodiment of the present invention and it is a plan view of the reaction region in its open state.

The detecting unit 1*i* shown in FIG. 9 has six pairs of opposing electrodes $E_1$-$E_7$, $E_2$-$E_8$, $E_3$-$E_9$, $E_4$-$E_{10}$, $E_5$-$E_{11}$, and $E_6$-$E_{12}$, which are arranged at regular intervals on the bottom $R_b$ of the reaction region (R).

The detecting unit 1*i* also has the fixing sites $F_1$ to $F_6$ which are independent of the electrodes and the application of electric field. The fixing sites $F_1$ to $F_6$ are held respectively between the opposing electrodes $E_1$-$E_7$, $E_2$-$E_8$, $E_3$-$E_9$, $E_4$-$E_{10}$, $E_5$-$E_{11}$, and $E_6$-$E_{12}$.

To operate the detecting unit 1*i*, the paired switches ($S_1$-$S_7$, $S_2$-$S_8$, $S_3$-$S_9$, $S_4$-$S_{10}$, $S_5$-$S_{11}$, and $S_6$-$S_{12}$) are turned on and off sequentially in the ascending or descending order. Application of electric fields in this manner moves the target nucleic acid T and hence permits efficient hybridization at individual fixing sites $F_1$ to $F_6$. It is also possible to apply an electric field across diagonally arranged electrodes (say, $E_1$ and $E_8$).

The detecting unit according to the tenth embodiment of the present invention will be described below with reference to FIG. 10, which is a plan view of the reaction region (R) in its open state.

Figure 10:
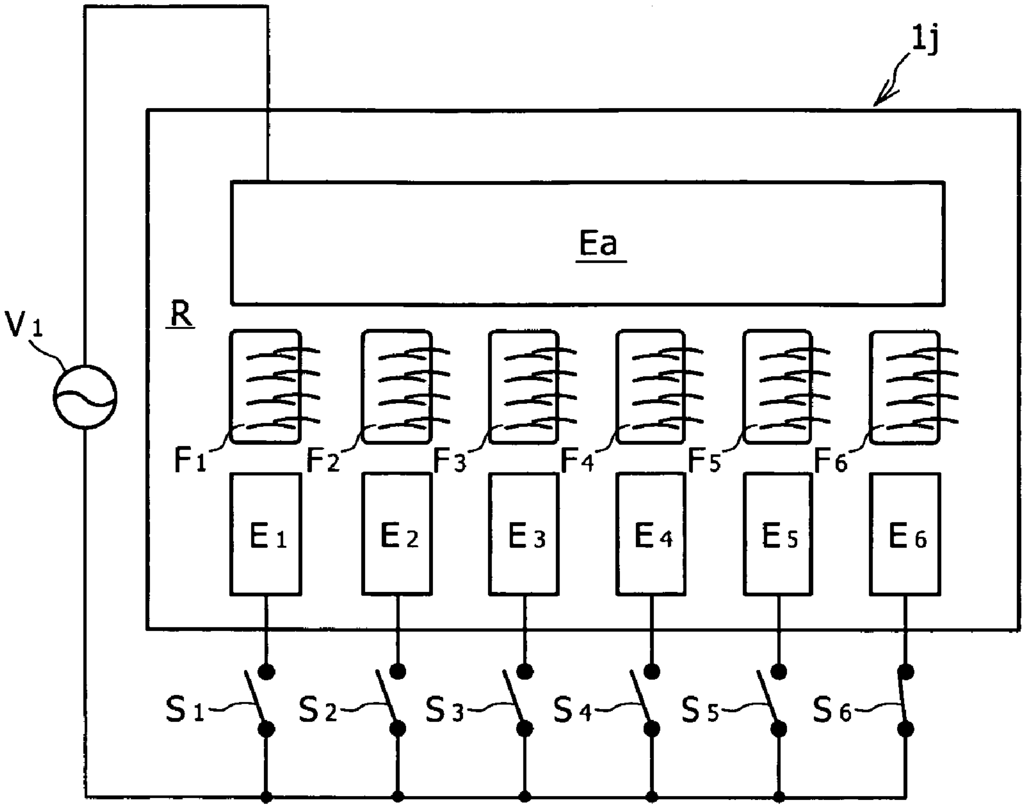
FIG. 10 is a diagram showing the structure of the detecting unit according to the tenth embodiment of the present invention and it is a plan view of the reaction region in its open state.

The detecting unit 1*j* shown in FIG. 10 has one common electrode $E_a$ and six electrodes $E_1$ to $E_6$ facing the common electrode $E_a$ (The number of electrodes is not limited to six). The fixing sites $F_1$ to $F_6$ (which are not electrodes) are held respectively between the opposing electrodes $E_1$-$E_a$, $E_2$-$E_a$, $E_3$-$E_a$, $E_4$-$E_a$, $E_5$-$E_a$, and $E_6$-$E_a$. The electrodes and the fixing sites are placed on the bottom $R_b$ of the reaction region (R).

The above-mentioned detecting units 1*a* to 1*j* have the common advantage that the target nucleic acid T is moved for efficient hybridization by the action of dielectrophoresis which is induced by sequential application of electric field to the opposing electrodes arranged in the reaction region (R).

According to the present invention, it is desirable to apply a high-frequency AC electric field to the medium in the reaction region (R). The high-frequency electric field should preferably be greater than 1 MV/m and 500 kHz, for example, about $1\times10^6$ V/m and about 1 MHz. (Refer to Masao Washizu and Osamu Kurosawa: "Electrostatic Manipulation of DNA in Microfabricated Structures", IEEE Transaction on Industrial Application, vol. 26, No. 26, p. 1165-1172 (1990).)

Incidentally, the medium containing a sample substance for assay may be surely introduced into the reaction region (R) by means of capillary action. To facilitate introduction of the medium, the reaction region (R) may be provided with the opening 21 and the air vent 22. In addition, the surface of the upper part of the opening 21 may be made hydrophobic for its better affinity with the medium.

The sensor chip according to the present invention may be prepared from one or more than one of any of the above-mentioned detecting units 1*a* to 1*j* which are arranged on a substrate of prescribed shape.

The method of dropping or injecting the medium into each reaction region (R) of the sensor chip is not specifically restricted. One way is by the ink jet printing technology, which injects the medium accurately to the reaction region (R) through a tiny jet nozzle whose position is controlled by an XYZ piezoelectric actuator.

Alternatively, the medium may be introduced into the reaction region (R) by the microspotting technology, which employs a microspotting pen, capillary, or print head with tweezers, whose position is controlled by an XYZ actuator.

The above-mentioned spotting methods permit tiny drops containing the detecting nucleic acid D or tiny drops containing the target nucleic acid D to be dropped accurately into the detecting units 3 on the substrate 1.

Figure 11:
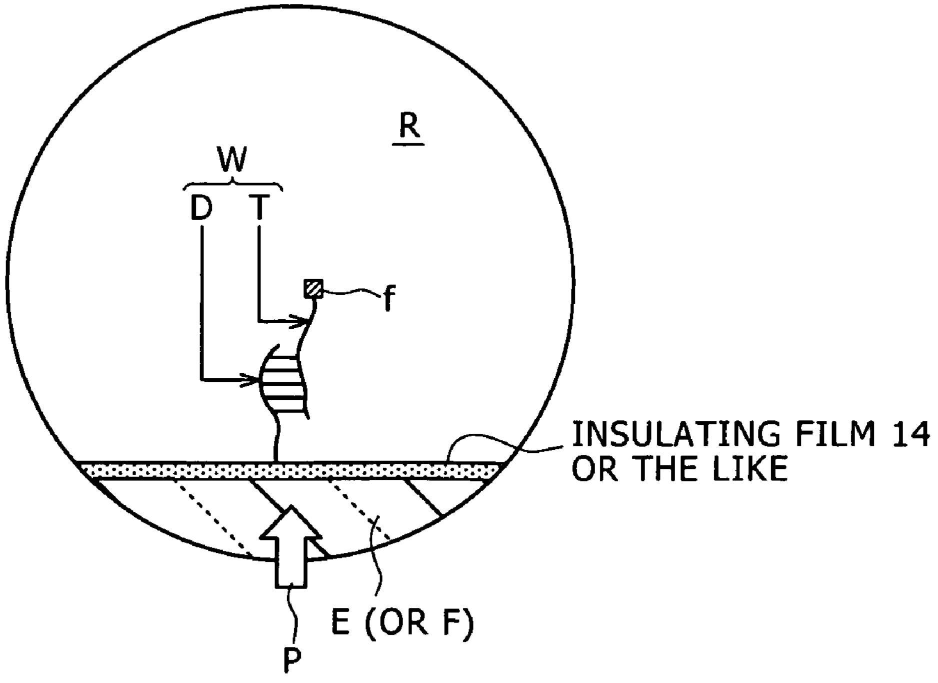
FIG. 11 is a conceptual diagram showing how to detect hybridization by labeling the target nucleic acid with a fluorescent substance.
Figure 12:
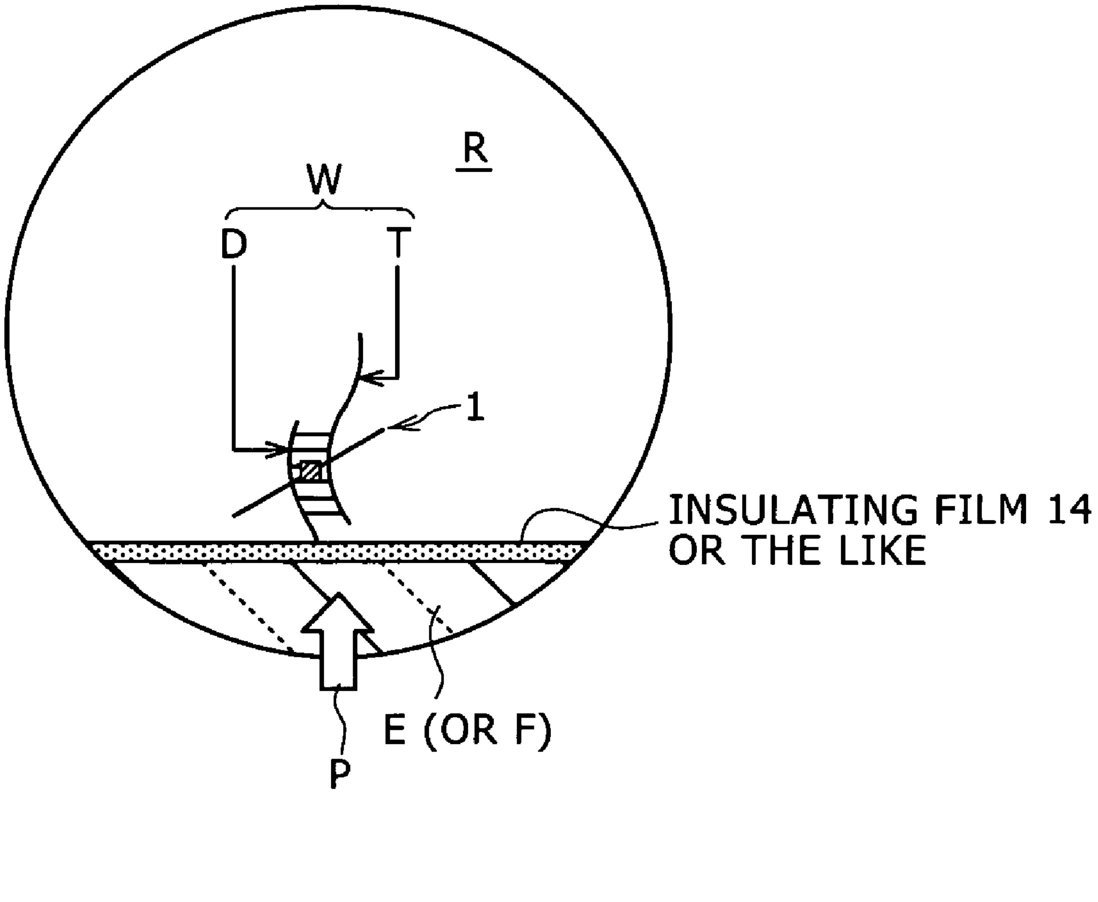
FIG. 12 is a conceptual diagram showing how to detect hybridization by means of a fluorescent intercalator.

Incidentally, hybridization can be detected by any known optical means to read the intensity of fluorescence produced by a fluorescent substance f (with which the target nucleic acid T has previously been labeled as shown in FIG. 11) or by an intercalator I (which specifically binds to the base pair of the double-stranded nucleic acid W as shown in FIG. 12). Hybridization may also be detected by using molecular beacons.

Hybridization may be detected by observation through either the upper side or lower side of the reaction region (R). As mentioned above, the detecting unit according to the present invention may be constructed such that the underlying layer 11 and the electrodes E are transparent to the laser beam P to read fluorescence (shown in FIGS. 11 and 12) which is directed to the reaction region (R) from below the substrate.

The present invention is applicable to the sensor chip, device, system, and method that permit accurate and rapid detection of hybridization.

What is claimed is:

1. A hybridization detecting unit, comprising:

a reaction region in which hybridization takes place, the reaction region having a top region and a bottom region, the reaction region being defined by a substrate in the bottom region, a defining layer on the substrate, and an upper layer in the top region on the defining layer, wherein the defining layer includes a well having a first side wall and a second side wall;

sites including first electrodes in the top region or the bottom region, the sites being in the well and having detection nucleic acids affixed thereto;

one or more second electrodes in the bottom region or the top region, the one or more second electrodes opposing the sites;

an opposed electrode in the first side wall; and an opposed electrode in the second side wall, one of the opposed electrodes being smaller than the other of the opposed electrodes.

2. The hybridization detecting unit as defined in claim 1, wherein the sites further include an insulating film formed on the first electrodes.

3. The hybridization detecting unit as defined in claim 1, wherein the one or more second electrodes includes a common electrode.

4. The hybridization detecting unit as defined in claim 1, wherein the one or more second electrodes comprises a plurality of electrodes opposing the first electrodes.

5. The hybridization detecting unit as defined in claim 4, wherein the plurality of second electrodes and the first electrodes are symmetrically arranged.

6. The hybridization detecting unit as defined in claim 4, further comprising an electric field generator coupled to the first electrodes and the plurality of second electrodes, the electric field generator sequentially applying an electric field in a prescribed direction to the first electrodes and the plurality of second electrodes.

7. The hybridization detecting unit as defined in claim 1 ,wherein the sites include nucleic acid molecules of the same species affixed thereto.

8. The hybridization detecting unit as defined in claim 1, wherein the sites include nucleic acid molecules of different species affixed thereto.

9. The hybridization detecting unit as defined in claim 1, further comprising an AC electric field generator coupled to the second electrode and the first electrodes, wherein the AC electric field generator applies an AC electric field to a medium retained in the reaction region to induce dielectrophoresis.

10. A sensor chip provided with the hybridization detecting unit defined in claim 1.

11. The hybridization detecting unit as defined in claim 1, wherein the upper layer comprises openings for introducing a target nucleic acid or an intercalator into the reaction region.

12. The hybridization detecting unit as defined in claim 1, wherein the substrate comprises a transparent material.

13. The hybridization detecting unit as defined in claim 1, wherein the upper layer comprises a light reflecting layer.

* * * * *